United States Patent
Bock et al.

(10) Patent No.: US 8,907,124 B2
(45) Date of Patent: Dec. 9, 2014

(54) PROCESS FOR PREPARING METHYLENEDI(PHENYL ISOCYANATE)

(75) Inventors: Michael Bock, Ruppertsberg (DE); Kai Thiele, Antwerp (BE); Heiner Schelling, Kirchheim (DE)

(73) Assignee: BASF SE, Ludwigshafen (DE)

( * ) Notice: Subject to any disclaimer, the term of this patent is extended or adjusted under 35 U.S.C. 154(b) by 197 days.

(21) Appl. No.: 13/299,039

(22) Filed: Nov. 17, 2011

(65) Prior Publication Data

US 2012/0123151 A1 May 17, 2012

Related U.S. Application Data (60) Provisional application No. 61/414,444, filed on Nov. 17, 2010.

(51) Int. Cl.
 *C07C 263/00* (2006.01)
 *C07C 263/10* (2006.01)
 *C07C 263/20* (2006.01)

(52) U.S. Cl.
 CPC ............. *C07C 263/10* (2013.01); *C07C 263/20* (2013.01)
 USPC .......................................... 560/253; 560/347

(58) Field of Classification Search
 CPC combination set(s) only.
 See application file for complete search history.

(56) References Cited

U.S. PATENT DOCUMENTS

| | | | |
|---|---|---|---|
| 3,912,600 A | 10/1975 | Hatfield, Jr. et al. | |
| 4,189,354 A * | 2/1980 | Ellendt et al. ................... | 203/81 |
| 4,465,638 A | 8/1984 | Kan et al. | |
| 5,364,958 A | 11/1994 | Ishida et al. | |
| 7,038,002 B2 * | 5/2006 | Pirkl et al. ....................... | 528/44 |
| 2005/0020797 A1 | 1/2005 | Pirkl et al. | |
| 2005/0222291 A1 | 10/2005 | Pirkl et al. | |
| 2007/0117997 A1 | 5/2007 | Keggenhoff et al. | |

FOREIGN PATENT DOCUMENTS

| | | |
|---|---|---|
| DE | 288598 | 12/1910 |
| DE | 288593 | 12/1913 |
| DE | 288599 | 10/1914 |
| DE | 1 938 384 | 3/1970 |
| DE | 1 923 214 | 11/1970 |
| DE | 26 31 168 | 1/1978 |
| DE | 103 33 929 A1 | 2/2005 |
| DE | 10 2005 004 170 A1 | 8/2006 |
| DE | 10 2005 055 189 A1 | 5/2007 |
| DE | 101003497 A | 7/2007 |
| EP | 0 079 516 | 5/1983 |
| EP | 0 116 847 | 8/1984 |

(Continued)

OTHER PUBLICATIONS

U.S. Appl. No. 13/434,135, filed Mar. 29, 2012, Lehr, et al.

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a process for preparing methylenedi (phenyl isocyanate), which comprises (a) the phosgenation of two-ring and/or multiring methylenedi(phenylamine), (b) the fractionation of the crude methylenedi(phenyl isocyanate) obtained to give two-ring and multiring isomers, (c) the purification and/or fractionation of the resulting mixture of two-ring isomers of methylenedi(phenyl isocyanate) and (d) the storage of the mixtures obtained in step (c) or in step (b), wherein part of the stored mixtures is reused by means of recirculation in at least one of steps (b) or (c).

20 Claims, 1 Drawing Sheet

(56) References Cited

FOREIGN PATENT DOCUMENTS

| | | |
|---|---|---|
| EP | 0 133 538 | 2/1985 |
| EP | 0 524 507 A1 | 1/1993 |
| EP | 0 866 057 A2 | 9/1998 |
| EP | 1 270 544 A1 | 1/2003 |
| EP | 1 449 826 A1 | 8/2004 |
| EP | 1 475 367 A1 | 11/2004 |
| EP | 1 506 957 A1 | 2/2005 |
| EP | 1 561 746 A2 | 8/2005 |
| EP | 1 616 857 A1 | 1/2006 |
| EP | 1 792 895 A1 | 6/2007 |
| JP | 6-345707 | 12/1994 |
| WO | WO 99/40059 A1 | 8/1999 |
| WO | WO 2004/056756 A1 | 7/2004 |
| WO | WO 2006/130405 A2 | 12/2006 |
| WO | WO 2008/006775 A1 | 1/2008 |
| WO | WO 2008/049783 A1 | 5/2008 |
| WO | WO 2010/121997 A1 | 10/2010 |
| WO | WO 2010/149544 A2 | 12/2010 |
| WO | WO 2011/006970 A1 | 1/2011 |
| WO | WO 2011/067369 A1 | 6/2011 |

OTHER PUBLICATIONS

U.S. Appl. No. 13/266,049, filed Oct. 24, 2011, Edkhard Stroefer, et al.
U.S. Appl. No. 13/296,665, filed Nov. 15, 2011, Michael Bock, et al.
European Search Report issued on Apr. 12, 2011 in corresponding European Application No. 10 19 1557 (with an English Translation of Categories).
U.S. Appl. No. 61/220,740, filed Jun. 26, 2009, Schelling, et al.
U.S. Appl. No. 13/380,680, filed Dec. 23, 2011, Schelling, et al.
U.S. Appl. No. 61/226,101, filed Jul. 16, 2009, Schelling, et al.
U.S. Appl. No. 13/383,549, filed Jan. 11, 2012, Schelling, et al.
U.S. Appl. No. 61/414,457, filed Nov. 17, 2010, Bock, et al.
U.S. Appl. No. 13/298,851, filed Nov. 17, 2011, Bock, et al.
U.S. Appl. No. 13/513,595, filed Jun. 4, 2012, Mattke, et al.

\* cited by examiner

PROCESS FOR PREPARING METHYLENEDI(PHENYL ISOCYANATE)

CROSS-REFERENCE TO RELATED APPLICATIONS

This application is based upon and claims the benefit of priority to U.S. Provisional Application No. 61/414,444 filed on Nov. 17, 2010.

BACKGROUND OF THE INVENTION

The invention relates to a process for preparing methylenedi(phenyl isocyanate), which comprises (a) the phosgenation of two-ring and/or multiring methylenedi(phenylamine), (b) the fractionation of the crude methylenedi(phenyl isocyanate) obtained to give two-ring and multiring isomers, (c) the purification and/or fractionation of the resulting mixture of two-ring isomers of methylenedi(phenyl isocyanate) and (d) the storage of the mixtures obtained in step (c) or in step (b), wherein part of the stored mixtures is reused by means of recirculation in at least one of steps (b) or (c).

Methylenedi(phenyl isocyanate) (MDI) is an important starting material for the preparation of polyurethanes and related polymers which are used, for example, in foams and coatings.

The acid-catalyzed preparation of methylenedi(phenyl isocyanate) (MDI) from aniline and formaldehyde is known and leads initially to a complex mixture of polyamines which is subsequently reacted with phosgene. Here, a complex mixture of two-ring and multiring MDI is initially obtained; this mixture will hereinafter be referred to as crude methylenedi(phenyl isocyanate) (crude MDI). Crude MDI comprises, in particular, the two-ring isomers 4,4'-MDI, 2,4'-MDI and smaller amounts of 2,2'-MDI (hereinafter referred to altogether as crude two-ring MDI) and also three-ring or multiring MDI, which will hereinafter be referred to as polymeric MDI (PMDI).

In known processes, crude MDI is separated into a PMDI-rich mixture and crude two-ring MDI. 4,4'-MDI and a 2,4'-MDI-rich mixture are then usually separated off from the crude two-ring MDI. Corresponding processes are described, for example, in the first publications DE 1923214, DE 102005004170, DE 102005055189, CN 101003497 and DE 10333929.

Before further processing, the liquid methylenedi(phenyl isocyanate) products prepared in this way have to be temporarily stored.

Methylenedi(phenyl isocyanate), in particular two-ring MDI, forms dimeric subsequent products in the liquid phase after some time, i.e. during storage. Here, the formation of uretdiones by 4-membered ring formation as a result of dimerization of two isocyanate groups and the formation of uretonimines by 4-membered ring formation from a carbodiimide group and an isocyanate group play a particularly important role. The formation of the 4-membered rings is basically an equilibrium reaction which can be shifted to the side of the isocyanates or carbodiimides by increasing the temperature. In the case of aromatic isocyanates, the formation of uretdiones also occurs in the absence of a catalyst. Trimerization to form isocyanurates (1,3,5-triazine-2,4,6-triones) is likewise possible but generally proceeds at an appreciable rate only on addition of a suitable catalyst.

The formation of the dimeric subsequent products which are insoluble in the methylenedi(phenyl isocyanate) leads to disadvantageous turbidity and sedimentation and results in reductions in quality in subsequent further processing, in particular due to blockage of lines, apparatuses and machines. Consequently, it is desirable to provide a process for preparing methylenedi(phenyl isocyanate) which avoids the abovementioned problems.

Processes for the redissociation of sediments in methylenedi(phenyl isocyanate) are known per se. EP 116847 A2 describes the preparation of crude methylenedi(phenyl isocyanate) from storage sediments. The sediment described there comprises dimeric methylenedi(phenyl isocyanate) (uretdione) and polymeric MDI dimers. These sediments are heated at from 180° C. to 250° C. in the presence of crude MDI for from 0.25 to 6 hours and subsequently cooled to a temperature of 60° C. or less in 5 minutes. The sediments which have been redissociated in this way can be used as crude methylenedi(phenyl isocyanate) for the production of polyurethane products. However, such a process carried out subsequent to the preparation of two-ring methylenedi(phenyl isocyanate) is complicated, for example because it requires a separation step and additional apparatuses. A process which reduces the formation of sediments without such separate redissociation processes would therefore be desirable.

It was therefore an object of the invention to discover a process for preparing methylenedi(phenyl isocyanate) which has the abovementioned disadvantages to only a small extent, if at all.

It was an object of the present invention to prepare MDI, in particular mixtures of 2,4'- and 4,4'-MDI and also pure 4,4'-MDI having a low content of uretdiones and uretonimines. The process should be able to be realized with a low outlay in terms of apparatus and employ mild conditions for MDI. The process should be able to be integrated into existing technologies for preparing two-ring MDI with a very small outlay in terms of process engineering. The process should reduce or prevent the formation of sediments and deposits during the storage of MDI and also increase the period of time for which the MDI can be stored without formation of sediments and deposits compared to the prior art.

The abovementioned objects are achieved by the process of the invention. Preferred embodiments may be found in the claims and the following description. Combinations of preferred embodiments of individual process steps do not go outside the scope of the present invention.

The process of the invention for preparing methylenedi(phenyl isocyanate) comprises the following steps:
(a) phosgenation of two-ring and/or multiring methylenedi(phenylamine) to give two-ring and/or multiring methylenedi(phenyl isocyanate),
(b) fractionation of the crude methylenedi(phenyl isocyanate) from step (a) to give at least one mixture M comprising two-ring isomers of methylenedi(phenyl isocyanate) and at least one mixture P comprising oligomeric methylenedi(phenyl isocyanate),
(c) purification and/or fractionation of at least one mixture M to give at least one further mixture F comprising at least one compound selected from among 2,2'-methylenedi(phenyl isocyanate), 2,4'-methylenedi(phenyl isocyanate) and 4,4'-methylenedi(phenyl isocyanate), and
(d) storage of the mixture F or mixtures F obtained in step (c) and also the mixture P obtained in step (b),
wherein part of at least one of the stored mixtures F and/or P is reused by means of recirculation in at least one of the steps (b) or (c).

The term "fractionation" refers to the partial or complete separation of a mixture into individual constituents or mixture constituents.

The term "purification" refers to the reduction of the content of secondary components in a mixture and thus an increase in the purity of a mixture in respect of a particular component.

"Storage" is the temporary storage of a material or mixture for the purpose of later use and/or dispensing. Storage is, in particular, the temporary storage of a material or mixture for a period of at least 1 day.

The term "recirculation" refers to the introduction of a particular amount of a material from a storage apparatus into a preceding step of the process for preparing MDI.

The term "distillation" or "distillative" refers to the purification of a mixture by means of a distillative separation process. In distillative separation processes, the separation action is based on the different compositions of the boiling liquid and the gaseous vapor.

For the purposes of the present invention, the content in ppm is basically in parts by weight based on the total weight of a mixture.

A column is an apparatus for the distillative purification of a mixture. For the purposes of the present invention, a column is a rectification column. Columns are known per se to those skilled in the art.

A column comprises a preferably elongated vessel having separation elements. Separation elements are internals which intensify heat transfer and mass transfer. The column additionally comprises a region below the lowermost separation element which can accommodate condensate (the bottom region) and a region above the uppermost separation element, viz. the top region. To vaporize the mixture to be separated, a vaporizer can be arranged below the bottom region of the rectification column. To condense the gas stream leaving the top region, a condenser can be connected downstream of the top of the column.

Depending on the type of separation elements used, a distinction is made between tray columns, columns having random packing and columns having ordered packing. The vaporized mixture of the materials to be separated is fed in through an inlet which is frequently located at the bottom of a column. As the mixture travels toward the top, it becomes enriched in the lower-boiling component and the latter can be taken off at the top, while the higher-boiling component is recirculated. The higher-boiling component accumulates in the bottom region and can be taken off there.

A distinction is usually made between three types of separation elements. In tray columns, sieve trays, bubble cap trays or valve trays are installed, and standing liquid is present on these. The vapor is bubbled into the liquid by means of specific slits or holes, so that a bubbling layer is formed. A new temperature-dependent equilibrium between the liquid phase and the gas phase is established on each of these trays.

Columns having random packing can be filled with various packing elements which bring about good distribution of the liquid and turbulent flow of the gas. As a result of the increase in surface area, heat exchange and mass transfer are optimized the separation power of the column is thus increased. Known examples are the Raschig ring (a hollow cylinder), Pall ring, Hiflow ring, Intalox saddle, Berl saddle and "hedgehog". The packing elements can be ordered, but are also introduced in a random fashion (as a bed) into the column.

Packed columns having ordered packing as separation elements (ordered packing elements) are a further development of the small packing elements arranged in an ordered manner. They have a regularly shaped structure. Ordered packing therefore makes it possible to reduce constrictions for the flow of gas (with a considerable influence on the pressure drop). There are various designs of ordered packing, e.g. mesh packing or metal sheet packing.

The condensation of aniline and formaldehyde to form crude methylenedi(phenylamine) (crude MDA) is adequately known from the prior art. Crude methylenedi(phenylamine) comprises two-ring and/or multiring methylenedi(phenylamine).

The industrial preparation of crude methylenedi(phenylamine) is generally carried out in two stages. In a first stage, an acid-catalyzed condensation of aniline with formaldehyde to produce the corresponding MDA mixture is firstly carried out. Here, a strong mineral acid such as aqueous hydrochloric acid is usually used as acid catalyst. Processes for preparing MDA by acid-catalyzed aniline-formaldehyde condensation are adequately known to those skilled in the art and are described, for example, in WO 99/40059.

The proportions of 4,4'-methylenedi(phenylamine) and the isomers and homologues thereof can be controlled by selection of the ratios of aniline, formaldehyde and mineral acid and also the temperature and residence time conditions. The condensation can be carried out either continuously or batchwise in industry. In a second stage, the reaction solution is preferably, advantageously after neutralization and phase separation, freed of water and aniline by distillation and worked up to give the crude methylenedi(phenylamine).

Step (a)

According to the invention, the phosgenation of two-ring and/or multiring methylenedi(phenylamine) is carried out in step (a) to give two-ring and/or multiring methylenedi(phenyl isocyanate). The phosgenation of MDA is well known to those skilled in the art. The MDA used will also be referred to as crude MDA, and the MDI resulting therefrom will also be referred to as crude MDI.

The reaction can be carried out either batchwise or continuously in the gas phase or in the liquid phase, as described in W. Siefken, Liebig Annalen der Chemie 562, 75 (1949). The continuous preparation of organic isocyanates by reactions of primary organic amines and phosgene has been described many times and is routine on the industrial scale and is described, for example, in Ullmanns Enzyklopadie der technischen Chemie, volume 7, third edition, Carl Hanser Verlag, p. 76 ff. (1993).

Present-day industrial syntheses of isocyanates are carried out virtually exclusively in continuous processes. In general, the continuous embodiment of the process is carried out in a plurality of stages. In the first stage of phosgenation, the amine is reacted with phosgene to form the corresponding carbamoyl chloride and hydrogen chloride and also amine hydrochlorides.

The primary reaction between amines and phosgene is very fast and exothermic. To minimize the formation of by-products and solids, amine and phosgene are mixed quickly, for example optionally dissolved in an organic solvent. The next stage of the phosgenation comprises both the decomposition of the carbamoyl chloride into the desired isocyanate and hydrogen chloride and also the phosgenation of the amine hydrochloride to form the carbamoyl chloride. Liquid-phase phosgenations are described, for example, in the first publications EP 1 616 857, WO 2004/056756, WO 2006/130405 and EP 012 70 544. To avoid the formation of the undesirable intermediate amine hydrochlorides, the phosgenation can also be carried out as a gas-phase phosgenation at high temperatures. Processes are described by way of example in the first publications EP 1 449 826 and WO 2008/006775 (aerosol phosgenation). Phosgenations in the supercritical region have also been described (WO 2008/049783).

In the process of the invention, the phosgenation can, for example, be carried out using a customary, preferably inert solvent. Suitable solvents are, for example, monochlorobenzene, dichlorobenzene or other chlorinated, aromatic hydrocarbons such as toluene or xylene. Temperatures of from 70 to 120° C. and pressures of from 8 to 5 bar are preferably set in the phosgenation. The phosgenation can be carried out in one or more stages. For example, the phosgenation can be carried out as a two-stage reaction in the presence of at least one inert organic solvent, with the first stage of the phosgenation taking place in a static mixer and the second stage of the phosgenation taking place in a residence apparatus.

Corresponding to the MDA used, the corresponding MDI isomers 2,2'-, 2,4'- and/or 4,4'-MDI and also PMDI are obtained by the phosgenation in the process of the invention.

After the phosgenation of the two-ring and/or multiring methylenedi(phenylamine), a work-up of the reaction mixture in which excess phosgene and solvent are separated off preferably takes place. In one possible embodiment, this can be followed by a physical, e.g. thermal, and/or chemical after-treatment to remove interfering by-products. Corresponding processes are likewise adequately known to those skilled in the art and are described, for example, in U.S. Pat. No. 3,912,600, DD 288599, U.S. Pat. No. 5,364,958, EP 0133538, JP 06345707, DD 288598, DD 288593, EP 0524507 and EP 0866057.

Step a) thus preferably gives a mixture of two- and/or multiring MDI comprising from 10 to 90% by weight, preferably from 20 to 75% by weight, particularly preferably from 30 to 60% by weight, of 4,4'-MDI, and also from 1 to 12% by weight, preferably from 2 to 10% by weight, particularly preferably from 4 to 9% by weight of 2,4'- and/or 2,2'-MDI and from 9 to 78% by weight, preferably from 23 to 70% by weight, particularly preferably from 36 to 61% by weight, of PMDI, in each case based on the total weight of the MDI mixture obtained.

Step (b)

According to the invention, the crude methylenedi(phenyl isocyanate) is subsequently fractionated in step (b) to give at least one mixture M comprising two-ring isomers of methylenedi(phenyl isocyanate) and at least one mixture P comprising polymeric methylenedi(phenyl isocyanate).

The mixture M will also be referred to as crude two-ring methylenedi(phenyl isocyanate) (MDI). Crude two-ring MDI is known to those skilled in the art as a mixture comprising 4,4'-methylenedi(phenyl isocyanate) together with at least one of the isomers 2,2'- and 2,4'-methylenedi(phenyl isocyanate). The mixture M preferably comprises from 80 to 100% by weight, in particular from 85 to 100% by weight, of two-ring MDI, with the two-ring MDI preferably comprising from 80 to 100% by weight, in particular from 85 to 95% by weight, of 4,4'-MDI, from 0 to 18% by weight, in particular from 5 to 14% by weight, of 2,4'-MDI and from 0 to 2% by weight, in particular from 0 to 1% by weight, of 2,2'-MDI, in each case based on the total weight of the mixture M.

The mixture P comprising polymeric methylenedi(phenyl isocyanate) (PMDI) preferably comprises from 40 to 80% by weight, in particular from 45 to 75% by weight, of PMDI and from 20 to 60% by weight, in particular from 25 to 55% by weight, of two-ring MDI.

Processes for fractionating crude methylenedi(phenyl isocyanate) are known to those skilled in the art. The fractionation can be carried out by known methods such as distillation, solvent extraction, extraction with supercritical media, e.g. supercritical $CO_2$, or crystallization. Preference is given to distillation and/or crystallization, which are described, for example, in the first publications DE 1938384, DE 2631168, EP 79516 and EP 1475367.

A distillative fractionation of the crude methylenedi(phenyl isocyanate) is preferably carried out in step (b) to give at least one mixture M comprising two-ring isomers of methylenedi(phenyl isocyanate) and at least one mixture P comprising oligomeric methylenedi(phenyl isocyanate). The distillative fractionation can in principle be carried out in various apparatuses. The distillative fractionation is preferably carried out in a convection vaporizer, in particular a falling film evaporator or forced circulation evaporator, or in boilers, in particular those of the kettle type. At a high degree of concentration, the distillative fractionation can also be carried out in thin film evaporators or helical tube evaporators. The fractionation can be carried out in one or more stages. In the case of a multistage embodiment, the abovementioned vaporizers are preferably bottom vaporizers of a distillation column.

In a particularly preferred embodiment, the fractionation is carried out by means of a falling film evaporator in step (b).

Step (c)

According to the invention, the purification and/or fractionation of at least one mixture M is carried out in step (c) to give at least one further mixture F comprising at least one compound selected from among 2,2'-methylenedi(phenyl isocyanate), 2,4'-methylenedi(phenyl isocyanate) and 4,4'-methylenedi(phenyl isocyanate).

The purification and/or fractionation of the mixture or mixtures M comprising two-ring isomers of methylenedi(phenyl isocyanate) is known per se to those skilled in the art. In step (c), the mixture M of the mixtures M is/are preferably fractionated to give at least two mixtures F which differ from the respective mixture M in the proportion of the isomers 4,4'-MDI, 2,4'-MDI and 2,2'-MDI.

In a preferred embodiment, at least one mixture F1 which has a higher content of 4,4'-MDI than the mixture M is obtained. The 4,4'-MDI content of the mixture F1 obtained is preferably at least 95% by weight, particularly preferably at least 97% by weight, in particular at least 98% by weight, based on the total weight of the mixture F1.

In this preferred embodiment, at least one further mixture F2 which has a lower content of 4,4'-MDI than the mixture M is obtained. The 2,4'-MDI content of the mixture F2 obtained is preferably at least 15% by weight, particularly preferably at least 20% by weight, in particular at least 25% by weight, based on the total weight of the mixture F2. At the same time, the content of 4,4'-MDI is preferably at least 15% by weight, particularly preferably at least 25% by weight, in particular at least 35% by weight, based on the total weight of the mixture F2.

The purification and/or fractionation of at least one mixture M to give at least one further mixture F comprising at least one compound selected from among 2,2'-MDI, 2,4'-MDI and 4,4'-MDI is preferably carried out by distillation, in particular by means of a distillation column (hereinafter referred to as column K2); it is optionally possible to use at least one further distillation column.

The mixture M of isomeric two-ring methylenedi(phenyl isocyanates) is preferably fed in (referred to as feed) into the column K2 at the side. The column K2 preferably comprises separation elements, with ordered packing being particularly suitable. It is in principle also possible to use random packing elements or trays. The column K2 is preferably a side column. For the present purposes, a side column is a column which has at least one bottom offtake, at least one side offtake and at least one top offtake.

Depending on the composition of the mixture, the temperature at the top of the column K2 is preferably from 165 to 200° C. The pressure at the bottom is preferably from 11 to 20 mbar at preferred temperatures of from 210 to 225° C. The column K2 preferably operates at a pressure at the bottom of from 0.1 to 50 mbar, more preferably from 1 to 30 mbar, particularly preferably from 2 to 15 mbar, and at a temperature at the bottom of from 150 to 250° C., particularly preferably from 180 to 240° C., in particular from 200 to 225° C. A high separation action combined with low thermal stressing is achieved in this way.

In the distillation of the mixture of isomeric methylenedi(phenyl isocyanates) in the column K2, 4,4'-methylenedi(phenyl isocyanate) having an isomer purity, i.e. a purity based on the three isomers 2,2'-MDI, 2,4'-MDI and 4,4'-MDI, of at least 97% is preferably taken off as a side stream (hereinafter referred to as first side stream or first side offtake stream).

In addition, a mixture of 2,4'-diisocyanatodiphenylmethane and 4,4'-diisocyanatodiphenyl-methane having a weight ratio of from 85:15 to 15:85 is obtained as second side offtake stream from a side offtake above the first side offtake or as overhead stream from the column K2 in the distillation of the mixture of isomeric methylenedi(phenyl isocyanates). The embodiment having a second side offtake above the first side offtake is preferred, since a high purity of the desired two-ring isomers is obtained in this way. The overhead stream from the column K2 additionally comprises the low-boiling components, e.g. monochlorobenzene, introduced with the feed.

The stream obtained at the second side offtake or at the top of the column K2 preferably has a 2,4'-MDI content of from 20 to 95% by weight and a 4,4'-MDI content of from 5 to 80% by weight, in each case based on the total weight of the two-ring isomers of methylenedi(phenyl isocyanate), which adds up to 100% by weight.

The column reflux ratio (ratio of runback stream to stream taken off) at the top of the column K2 is, in particular, set in the range from 10 to 250, but is particularly preferably in the range from 60 to 120, with the distillate stream amounting to from 1 to 5% by weight based on the feed stream. The bottom stream is from 60 to 90% by weight, preferably from 75 to 85% by weight, of the feed stream.

In a first preferred embodiment, the column K2 is a dividing wall column. The structure of such a column K2 is known per se to those skilled in the art and is described, for example, in EP 1475367 A1, the contents of which are fully incorporated by reference. The dividing wall column is preferably operated under conditions indicated above for the column K2. The mixture M of isomeric two-ring methylenedi(phenyl isocyanates) is preferably fed in at the side in the region of the dividing wall in the dividing wall column. The region of the dividing wall is located in the middle region of the column K2. The length of the dividing wall is selected as a function of the process conditions and of the properties of the mass transfer elements used. The dividing wall divides the column into a prefractionation zone and a main fractionation zone. Ordered packings are particularly suitable as separation elements. However, it is in principle also possible to use random packing elements or trays.

As an alternative, the distillative isolation of the two-ring MDI isomers can also be carried out in two stages, with a first distillation stage being carried out in a distillation column without a dividing wall and a second stage being carried out using a dividing wall column or with two dividing wall columns being used. Corresponding processes are described in EP 1475367 A1 in paragraphs [0024] to [0031].

In a second preferred embodiment, the column K2 is a side column without a dividing wall. The preferred parameters of the side column have been described above. Here, 2,2'-MDI and low boilers are preferably separated off by means of the top offtake and 4,4'-MDI and high boilers are preferably separated off by means of the bottom offtake, with the stream taken off at the top and the bottom being able to be reused in step (b) of the process of the invention. As described above, 4,4'-MDI is preferably taken off from the side column in a purity of at least 97% by weight, based on the total weight of the stream, at a first side offtake and the above-described mixture of 4,4'-MDI and 2,4'-MDI is preferably taken off at a second side offtake above the first side offtake.

In a particularly preferred embodiment, the above-described mixture F1 is obtained from a further column K1 located downstream of the column K2. In this particularly preferred embodiment, step (c) is carried out as follows.

A mixture I is taken off from the column K2, preferably as side stream, and fed in gaseous form to the column K1. The mixture I is 4,4'-MDI having a purity of preferably at least 98% by weight, particularly preferably from 98.5 to 99.0% by weight, based on the total weight of the mixture I.

In the column K1, the gas stream comprising the mixture I is preferably brought into contact with at least one liquid compound A which has a boiling point equal to or higher than that of 4,4'-methylenedi(phenyl isocyanate) and preferably has a content of aromatic halogen compounds of not more than 50 ppm.

In principle, possible liquid compounds A are compounds which are either inert toward 4,4'-methylenedi(phenyl isocyanate) or are 4,4'-methylenedi(phenyl isocyanate) itself, with the content of aromatic halogen compounds in each case preferably being not more than 50 ppm, in particular not more than 40 ppm, particularly preferably not more than 30 ppm, in particular not more than 20 ppm, very particularly preferably not more than 10 ppm.

Suitable inert compounds A are, in particular, dibenzyl ether, terphenyl, higher phthalic esters, naphthalene derivatives. It is of course also possible to use mixtures of the abovementioned inert compounds.

However, the compound A is particularly preferably 4,4'-methylenedi(phenyl isocyanate). Particular preference is given to using 4,4'-methylenedi(phenyl isocyanate) having a purity of at least 97% by weight, particularly preferably at least 98% by weight, in particular at least 98.5% by weight, as compound A. However, it is in principle also possible to use a mixture of 4,4'-methylenedi(phenyl isocyanate) of the abovementioned purity with at least one of the abovementioned inert compounds.

The compound A is particularly preferably 4,4'-methylenedi(phenyl isocyanate) which is recirculated as per step (d) according to the invention. In this way, a proportion of 4,4'-methylenedi(phenyl isocyanate) which has already passed through the process of the invention and has to be stored in a suitable way is fed back to the process. Two advantages can at the same time be realized as a result: firstly, 4,4'-MDI which is low in aromatic halogen compounds is made available according to the invention and, secondly, stored 4,4-MDI which was partly degraded to form subsequent products as a result of storage is recycled and goes in high-purity form to storage, as a result of which the quality of the stored 4,4'-MDI can be optimized according to the invention (avoidance of sediments and deposits). Here, the storage recycle ratio (ratio of the amount of 4,4'-MDI recirculated to the amount of 4,4'-MDI freshly added to storage (additional amount obtained)) is preferably from 0.05 to 0.4, in particular from 0.1 to 0.3.

Very particular preference is given to 4,4'-methylenedi(phenyl isocyanate) being recirculated from a facility for the storage of 4,4'-methylenedi(phenyl isocyanate). A facility for storage is in this case any facility which is provided for the temporary accommodation of the material or mixture to be stored, preferably a container, in particular a storage tank.

The introduction of the liquid compound A is preferably effected above the uppermost separation element of the column K1. In a preferred embodiment, the column K1 is a column having ordered packing. The specific surface area of the packing is preferably from 100 to 1000 $m^2/m^3$, particularly preferably from 150 to 800 $m^2/m^3$, in particular from 200 to 750 $m^2/m^3$, very particularly preferably from 250 to 600 $m^2/m^3$.

Preference is given in principle to packings which cause a low pressure drop. Suitable packings are, for example, mesh packings, metal sheet packings and structured packings. Mesh packings are particularly preferred. The liquid compound A is in this case preferably introduced above the uppermost packing element of the column K1.

It is in principle possible to use a number of methods of contacting. Preference is given to methods which lead to intensive contact of the gas stream and the liquid compound A. For this purpose, the liquid A has to be distributed in a suitable way. Appropriate methods are known per se to those skilled in the art.

The effectiveness of contacting depends, in particular, on uniform, area-covering introduction of liquid. Liquid distributors ensure a largely homogeneous liquid distribution over the cross section of the column and are known to those skilled in the art. Predistribution of the liquid can be achieved by means of one or more feed tubes or distributor channels having a plurality of outflow openings located on the underside.

An important design parameter is the number of introduction points based on the column cross section (=droplet introduction density). The following types of liquid distributors are possible: distributor trays, channel distributors, tube distributors and nozzle distributors. The following principles of liquid distribution are possible: bank-up height distribution via holes in the bottom of distributors or introduction tubes having drilled holes along the side, overflow distribution, e.g. via lateral slits or overflow spouts and nozzles.

Suitable liquid distributors are, in particular, box channel distributors. It is advantageous for contacting to be carried out in countercurrent to the gas stream I. This gives a particularly low content of aromatic halogen compounds in the resulting mixture.

The absolute pressure at the top of the column K1 is preferably not more than 50 mbar, particularly preferably from 1 to 30 mbar, in particular from 2 to 20 mbar. The pressure difference between top and bottom (pressure drop) of the column K1 is preferably from 0.5 to 30 mbar, preferably from 0.5 to 20 mbar, particularly preferably from 1 to 10 mbar, in particular from 2 to 5 mbar. A low pressure drop brings about lower thermal stress on the product due to relatively low temperatures in the bottom region.

The temperature in the bottom region of the column K1 is from 140 to 270° C., preferably from 150° C. to 240° C., particularly preferably from 170 to 230° C., in particular from 190 to 230° C., very particularly preferably from 200 to 225° C. This minimizes the thermal stress at a given efficiency of purification.

The reflux ratio, here defined as the ratio of scrubbing liquid to vapor S:V [w/w] is S:V=0.01 to 2.0, preferably S:V=0.05 to 0.5, particularly preferably S:V=0.1 to 0.3.

The column K1 can be made of various materials as long as the materials used are inert to the mixtures used at the given temperature. Suitable materials are, in particular, austenitic stainless steels such as 1.4541 or 1.4571. High-alloy materials such as the ferritic/austenitic 1.4462 are also suitable. Preference is given to using the material 1.4541.

A stream O which consists of the purified mixture comprising 4,4'-methylenedi(phenyl isocyanate) and preferably has a content of aromatic halogen compounds of not more than 50 ppm is obtained at the top of the column K1. The stream O is subsequently subjected to cooling by cooling the stream O to a temperature of preferably from 10 to 100° C., in particular from 20 to 80° C., in particular from 20 to 60° C.

Cooling of the stream O is preferably effected in not more than 5 seconds from the temperature at the top of the column K1 to a temperature in the range from 20° C. to 60° C., preferably from 30° C. to 50° C. The rapid cooling further reduces the formation of subsequent products, in particular the formation of dimeric subsequent products.

Step (d)

According to the invention, the mixture F or mixtures F obtained in step (c) and the mixture P obtained in step (b) are stored in step (d), with part of at least one of the stored mixtures F and/or P being reused by means of recirculation in at least one of the steps (b) or (c).

The amount recirculated from storage to the process can in principle vary over a wide range. If only a small amount, based on the total amount of the respective MDI mixture fed to storage, is recirculated, the formation of sediments may not be able to be prevented completely. Recirculation of a high proportion, on the other hand, is often not economical.

The amount of the mixtures F and/or P recirculated from storage, based on the total amount of the mixtures F and/or P fed to storage, is preferably from 1 to 30% by weight, preferably from 5 to 25% by weight, in particular from 10 to 20% by weight.

An advantage of the recirculation is that the compounds which form sediments and/or deposits in MDI, in particular uretonimines and uretdiones, redissociate without establishing an additional process step.

The recirculation of the stored mixtures F or P is accordingly preferably carried out at a point of reintroduction at which the temperature and residence time are such that redissociation of uretdione units into isocyanate units occurs. The recirculation is preferably carried out in such a way that the mixture is reintroduced at a point which is characterized as follows: T>190° C., residence time at this temperature from 5 to 30 minutes.

In addition, the recirculation of the stored mixtures F or P is preferably carried out at a point of reintroduction at which the temperature and residence time are such that redissociation of uretonimine units into isocyanate and carbodiimide units occurs. The recirculation is preferably carried out in such a way that the mixture is reintroduced at a point which is characterized as follows: T>190° C., residence time at this temperature from 5 to 30 minutes.

The recirculation of the stored mixtures F and/or P can be carried out continuously (continual recirculation of a particular proportion of the stored mixture) or discontinuously.

In a first preferred embodiment, the recirculation of the stored mixtures F and/or P is carried out within a continuous process. The amount of the mixtures F and/or P recirculated continuously from storage, based on the total amount of the mixtures F and/or P fed to storage, is preferably from 1 to 30% by weight, preferably from 5 to 25% by weight, in particular from 10 to 20% by weight.

In a second preferred embodiment, the recirculation of the stored mixtures F and/or P is carried out within a batch process, preferably when a content of more than 0.5% by weight of uretdione has been reached, particularly preferably when a content of more than 0.3% by weight of uretdione has been reached, calculated as dimeric methylenedi(phenyl isocyanate) unit based on the total weight of the stored methylenedi(phenyl isocyanate). The amount of the mixtures F and/or P recirculated discontinuously from storage, based on the total amount of the mixtures F and/or P fed to storage, is preferably from 1 to 30% by weight, preferably from 5 to 25% by weight, in particular from 10 to 20% by weight.

The storage temperature controls the kinetics of the formation of uretdiones and uretonimines. The temperature of the stored mixtures F and/or P is preferably from 5 to 60° C., particularly preferably from 10 to 50° C., particularly preferably from 15 to 45° C., in particular from 20 to 45° C.

The duration of storage is with preference at least 1 day, in particular at least 2 days, preferably at least 3 days, particularly preferably at least 5 days. In some cases, the duration of storage is even at least 1 week, in particular at least 2 weeks. The upper limit of storage is determined by the chemical change of the mixture stored, which is not entirely avoidable, and is in particular at most 4 weeks, preferably at most 3 weeks, in particular at most 2 weeks. Those skilled in the art will choose the quantity recirculated from storage in a suitable manner together with the storage temperatures mentioned. The durations of storage mentioned can advantageously be realized in combination with the storage temperatures also mentioned.

The preferred location of reintroduction or the process step in which the recirculated MDI mixture is reused also depends on the composition, i.e. on whether the mixture concerned is the mixture P or a mixture F. Corresponding preferred embodiments are described below.

Of course, the mixtures P and F obtained can be recirculated independently of one another, in particular fed into different facilities or reused in different process steps.

In a first preferred embodiment, at least part of the stored mixture P is reused in step (b) by means of recirculation. Preference is given to recirculating at least part of the stored mixture P to a separation apparatus, preferably a column or a vaporizer, in particular a thin film evaporator or a falling film evaporator, used in step (b).

The recirculated part of the stored mixture P is preferably recirculated to the pump circuit of a falling film evaporator for separation of crude methylenedi(phenyl isocyanate) into the mixtures M and P.

In a further preferred embodiment, at least one mixture F1 comprising at least 95% by weight of 4,4'-methylenedi(phenyl isocyanate), based on the total weight of the mixture F1, is recirculated and reused in step (c). Mixtures F1 have been described in detail above.

The 4,4'-methylenedi(phenyl isocyanate) content of the recirculated mixture F1 is preferably at least 97% by weight, preferably at least 98% by weight, in particular at least 99% by weight, based on the total weight of the recirculated mixture F1.

Particular preference is given to at least one mixture F1 being recirculated to the above-described column K2 for the distillative fractionation of the mixture M and reusing it in step (d). The reintroduction preferably occurs either at the same point as the introduction of the feed or below the point of introduction of the feed.

In a very particularly preferred embodiment, the above-described mixture F1 is recirculated to a column K1 for the distillative purification of 4,4'-methylenedi(phenyl isocyanate), with said distillative purification of 4,4'-methylenedi(phenyl isocyanate) being carried out subsequent to the distillative fractionation of the mixture M by means of the above-described column K2.

The recirculation is preferably effected in liquid form as compound A as described above for step (c) above the uppermost separation element of the column K1.

In a further preferred embodiment, at least one stored mixture F2 comprising 4,4'-methylenedi(phenyl isocyanate) and 2,4'-methylenedi(phenyl isocyanate) is recirculated in a column K2 for the distillative fractionation of a mixture M in step (c). The reintroduction is preferably effected at the same point as the introduction of the feed to the column K2 (inlet stream of two-ring MDI isomers) or above the point at which said feed is introduced. Mixtures F1 have been described in detail above.

Figure 1:
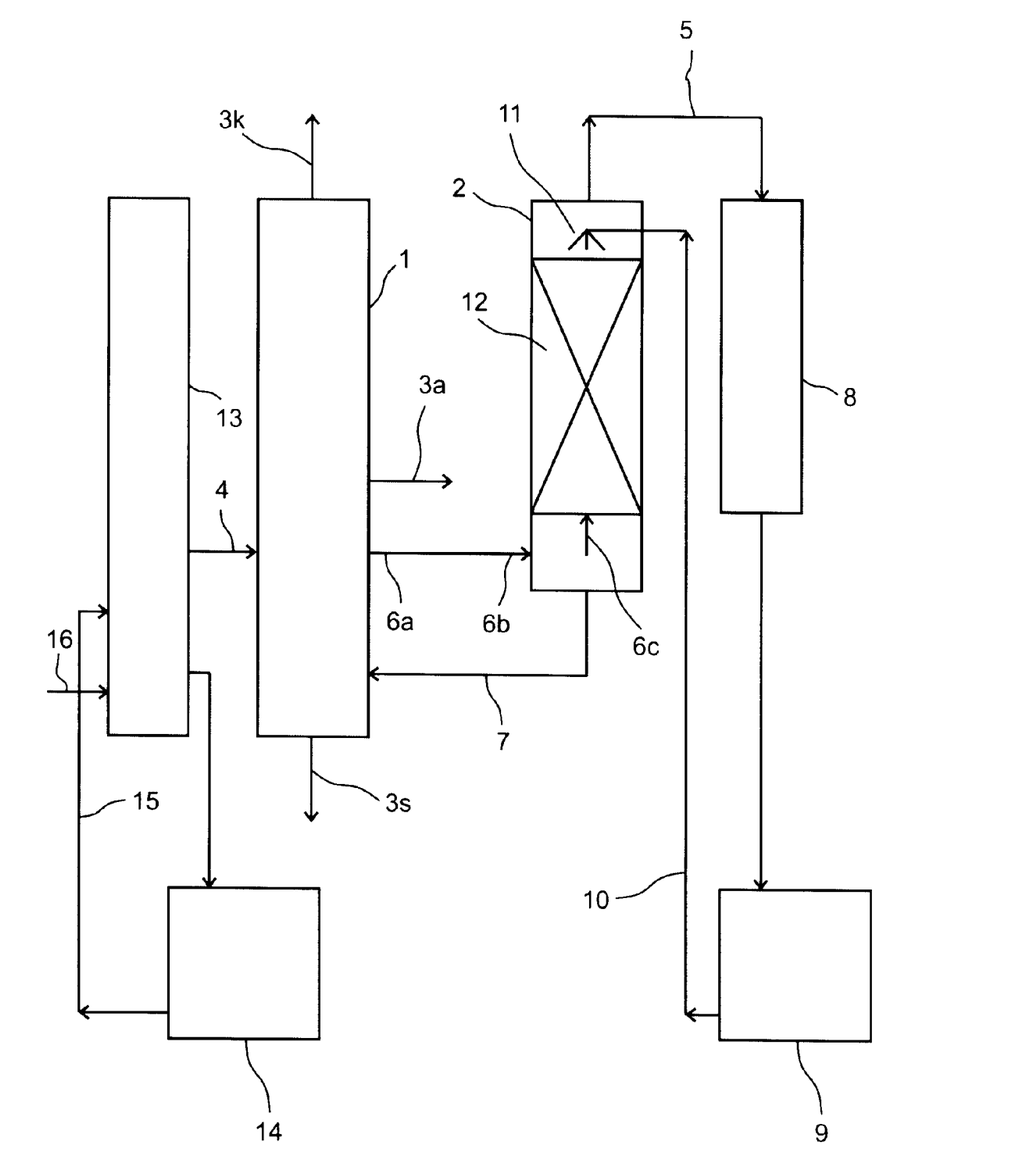

A preferred embodiment of the present invention is shown schematically in FIG. 1. FIG. 1 serves to illustrate this preferred embodiment of the present invention and is not to be construed as a limitation. Individual elements of the preferred embodiments described below can advantageously be combined with embodiments described above.

In FIG. 1, the reference numerals have the following meanings:
1—column K2
2—column K1
3a—upper side offtake stream from the column K2
3k—overhead stream from the column K2
3s—bottom stream from the column K2
4—stream of 2-ring MDI isomers (feed to column K2)
5—overhead stream O from the column K1
6a—lower side offtake stream from the column K2
6b—stream of mixture I
6c—vapor of mixture I
7—bottom stream from column K1
8—condenser
9—storage tank for liquid 4,4'-MDI
10—recirculation from storage tank
11—liquid distributor
12—packing elements
13—apparatus for separating off 2-ring MDI and PMDI
14—storage tank for liquid PMDI
15—recirculation of PMDI
16—crude MDI feed Description of the Preferred Embodiment as per FIG. 1:

The crude MDI feed (16) is firstly fed into an apparatus (13) for separating off the two-ring isomers of MDI and also a mixture comprising PMDI. The apparatus (13) is preferably a falling film evaporator. The liquid PMDI obtained after the separation, optionally after condensation and/or heat exchange, is fed to a storage tank (14). The recirculation (15) according to the invention of the stored PMDI-comprising mixture to the apparatus (13) is preferably effected above the point at which the feed (15) is introduced. A stream (4) comprising a mixture of two-ring isomers of MDI is fed to the column K2 (1). The bottom stream (3s) is obtained at the bottom of the column K2 (1) and the overhead stream (3k) is obtained at the top. A stream (6b) which preferably comprises at least 98% by weight of 4,4'-MDI is taken off from a first stream (6a), and a stream (3a) comprising 4,4'-MDI and 2,4'-MDI is taken off at a point above the point at which the first side stream is taken off. The stream (6b) forms the stream I which is fed in the gaseous state to the column K1 (2) and passes as vapor comprising the mixture I (6c) through the packing elements (12) of the column K1 (2). 4,4'-MDI which has been taken from a storage tank (9) for liquid 4,4'-MDI and is fed via a recirculation line (10) to a liquid distributor (11) at the top of the column K1 travels in countercurrent to the stream (6c). The liquid distributor (11) ensures a high contact area between the ascending gaseous stream (6c) and the liquid stream of 4,4'-MDI travelling in countercurrent. At the bottom of the column K1 (2), the stream (7) is obtained and is recirculated to the column K2 (1). At the top of the column K1, the overhead stream O (5) of purified 4,4'-MDI is obtained. The gaseous stream (5) is fed to a condenser (8) in which the stream (5) is condensed. The high-purity liquid 4,4'-MDI obtained in this way is subsequently fed to a storage tank (9).

EXAMPLES

Example 1

(According to the Invention)

An apparatus as shown schematically in FIG. 1 was used.

2.0 kg/h of crude MDI comprising 50.2% by weight of 4,4'-MDI, 6.8% by weight of 2,4'-MDI, 21.2% by weight of 3-ring MDI were vaporized at a pressure of 5 mbar in a falling film evaporator made of the material 1.4571.

After condensation, a distillate comprising 85.1% by weight of 4,4'-MDI, 12.6% by weight of 2,4'-MDI, 2.3% by weight of 3-ring MDI was obtained. The mass flow of the distillate condensed at the condenser was 0.690 kg/h.

The distillate was fed in liquid form to a side offtake column K2. The column K2 and the bottom vaporizer were made of the material 1.4571. The column was equipped with structured packing which had a low pressure drop. The pressure at the top of the column was 5 mbar.

The column K2 comprised an enrichment section and a stripping section. The stream I was taken off in gaseous form from the stripping section of the column K2 by means of a first side offtake (6a) below a packing element and was fed to the column K1 (stream of mixture I). The bottom output from the column K1 (7) was fed to the column K2 at a point below the point at which the feed was introduced into the column K2. Above the feed point, a liquid fraction was taken off at an upper side offtake (3a).

The stream I (6b) comprised 98.7% by weight of 4,4'-MDI and 1.3% by weight of 2,4'-MDI. The content of 3-ring compounds was 530 ppm. The mass flow of the stream (6) was 0.79 kg/h. A mixture of 47% by weight of 4,4'-MDI and 53% by weight of 2,4'-MDI was taken off as stream (3k). The mass flow was 0.14 kg/h.

Purification of side stream (6): the gaseous side stream (vapor of mixture I, 6c) was fed to the column K1 (2). The column K1 made of the material 1.4571 was equipped with a low-pressure-drop packing (structured) having a specific surface area of 500 m²/m³. The pressure at the top of the column was 15 mbar.

Introduction of the liquid compound A: a stream of the compound A comprising 98.5% by weight of 4,4'-MDI and 1.5% by weight of 2,4'-MDI was introduced in liquid form at the top of the column K1 above the uppermost packing element and was distributed by means of a box channel liquid distributor (11). The mass flow of the compound A was 0.17 kg/h. The liquid A comprised 4,4'-MDI which had been stored at 42° C. from a storage tank (9) in which high-purity 4,4'-MDI which had already passed through the process was accommodated. The dimer content of the compound A was 0.13% by weight. The weight ratio of product recirculated to column K1 to the product fed to the storage tank was continuously 0.26.

A gaseous stream O (5) comprising 98.5% by weight of 4,4'-MDI and 1.5% by weight of 2,4'-MDI was obtained as product at the top of the column K1. The mass flow here was 0.65 kg/h. The stream O (5) was cooled to 42° C. within 5 s in a condenser (8) and fed to the storage tank (9).

The invention claimed is:

1. A process for preparing a methylene diphenyl isocyanate), the process comprising:
    (a) phosgenation of a crude MDA mixture to form a crude MDI mixture;
    (b) fractionation of the crude MDI mixture to give at least one crude two-ring MDI mixture M and at least one polymeric MDI mixture P;
    (c) purification and/or fractionation of at least one mixture M to give at least one mixture F comprising at least one selected from the group consisting of 2,2'-MDI, 2,4'-MDI and 4,4'-MDI; and
    (d) independent storage of the mixture F obtained in step (c) and the mixture P obtained in step (b), to obtain a stored mixture F and a stored mixture P,
    wherein 1 to 30% by weight of the stored mixture F and/or part of the stored mixture P based on a total amount of the mixture F and/or the mixture P independently stored is, independently, recirculated to at least one of the steps (b) or (c).

2. The process according to claim 1, wherein the independent recirculation of the stored mixture F and/or the stored mixture P occurs at a point at which redissociation of uretdione units into isocyanate units occurs, based on a storage temperature and a residence time of the stored mixture F and/or the stored mixture P.

3. The process according to claim 1, wherein the independent recirculation of the stored mixture F and/or the stored mixture P occurs at a point at which redissociation of uretonimine units into isocyanate and carbodiimide units occurs, based on a storage temperature and a residence time of the stored mixture F and/or the stored mixture P.

4. The process according to claim 1, wherein the stored mixture F and/or the stored mixture P are continuously recirculated.

5. The process according to claim 1, wherein the stored mixture F and/or the stored mixture P are batch recirculated.

6. The process according to claim 1, wherein a temperature of the stored mixture F and/or the stored mixture P ranges from 5° C. to 60° C.

7. The process according to claim 1, wherein at least part of the stored mixture P is recirculated to the fractionation step (b).

8. The process according to claim 7, wherein at least part of the stored mixture P is recirculated to a separation apparatus of the fractionation step (b).

9. The process according to claim 7, wherein the stored mixture P is recirculated to a pumped circuit of a falling film evaporator in the fractionation step (b).

10. The process according to claim 1, wherein:
    the purification and/or fractionation (c) of the at least one mixture M gives at least one mixture F1 comprising at least 95% by weight of 4,4'-MDI, based on a total weight of the mixture F;
    the at least one mixture F1 is independently stored to obtain a stored mixture F1; and
    the stored mixture F1 is recirculated to the purification and/or fractionation step (c).

11. The process according to claim 10, wherein the 4,4'-MDI content of a recirculated mixture F1 is at least 97% by weight, based on the total weight of the recirculated mixture F.

12. The process according to claim 10, wherein at least one stored mixture F1 is recirculated to at least one column K2 for a distillative fractionation of the mixture M in the step (c).

13. The process according to claim 10, wherein at least one stored mixture F1 is recirculated to a column K1 for a distillative purification of 4,4'-methylenedi(phenyl isocyanate), with said distillative purification of 4,4'-methylenedi(phenyl isocyanate) occurring after the distillative fractionation of the mixture M with at least one column K2 in the purification and/or fractionation step (c).

14. The process according to claim 13, wherein the recirculation of the at least one stored mixture F1 occurs in liquid form to above an uppermost separation element of the column K1.

15. The process according to claim 10, wherein from 1 to 30% by weight of the stored mixture F1, based on a total weight of the stored mixture F1, is recirculated.

16. The process according to claim 1, wherein:
the purification and/or fractionation (c) of the at least one mixture M gives at least one mixture F2 comprising 4,4'-MDI and 2,4'-MDI and having a lower content of 4,4'-MDI than the at least one mixture M;
the at least one mixture F2 is stored; and
a stored mixture F2 is recirculated to a column K2 for a distillative fractionation of the mixture M in step (c).

17. The process of claim 8, wherein the separation apparatus is a column or a vaporizer.

18. The process of claim 8, wherein the separation apparatus is a thin film evaporator or a falling film evaporator.

19. The process of claim 1 wherein 5 to 25% by weight is recirculated.

20. The process of claim 1 wherein 10 to 20% by weight is recirculated.

* * * * *